(12) United States Patent
Paradis

(10) Patent No.: US 11,903,726 B2
(45) Date of Patent: Feb. 20, 2024

(54) SYSTEM FOR DYNAMICALLY STABILIZING THE CHEST WALL AFTER INJURY, FRACTURE, OR OPERATIVE PROCEDURES

(71) Applicant: Norman A. Paradis, Putney, VT (US)

(72) Inventor: Norman A. Paradis, Putney, VT (US)

( * ) Notice: Subject to any disclaimer, the term of this patent is extended or adjusted under 35 U.S.C. 154(b) by 0 days.

(21) Appl. No.: 17/532,992

(22) Filed: Nov. 22, 2021

(65) Prior Publication Data
US 2022/0079517 A1    Mar. 17, 2022

Related U.S. Application Data

(63) Continuation of application No. 15/051,383, filed on Feb. 23, 2016, now Pat. No. 11,179,098.
(Continued)

(51) Int. Cl.
| | |
|---|---|
| *A61B 5/00* | (2006.01) |
| *A61B 5/05* | (2021.01) |
| *A61B 5/113* | (2006.01) |
| *A61B 5/08* | (2006.01) |
| *A61H 9/00* | (2006.01) |

(Continued)

(52) U.S. Cl.
CPC .............. *A61B 5/4836* (2013.01); *A61B 5/08* (2013.01); *A61B 5/1135* (2013.01); *A61H 9/0078* (2013.01); *A61H 31/02* (2013.01); *A61H 2031/002* (2013.01); *A61H 2201/0103* (2013.01); *A61H 2201/1238* (2013.01); *A61H 2201/5087* (2013.01); *A61H 2230/405* (2013.01); *A61H 2230/655* (2013.01)

(58) Field of Classification Search
CPC ....... A61B 5/4836; A61B 5/08; A61B 5/1135; A61H 9/0078; A61H 31/02; A61H 2031/002; A61H 2201/0103; A61H 2201/1238; A61H 2201/5087; A61H 2230/405; A61H 2230/655
See application file for complete search history.

(56) References Cited

U.S. PATENT DOCUMENTS 4,257,407 A * 3/1981 Macchi .................. A61H 31/02
                                                                                              601/44
5,222,478 A * 6/1993 Scarberry ......... A61M 16/0605
                                                                                              601/44
(Continued)

*Primary Examiner* — Quang D Thanh
(74) *Attorney, Agent, or Firm* — Nathaniel A. Wickliffe

(57) ABSTRACT

A device for treating chest wall injuries, including rib fractures, flail chest injuries or surgical incisions is described herein. The device includes a localized airtight compartment external to the chest wall and fully covering the area of injury, and is capable of varying the pressure within the compartment, and providing dynamic real-time counter forces that act reciprocal to the intrathoracic pressure changes that occur during ventilation. In a preferred embodiment, the device has the capability of sensing the patient's chest wall motion created by ventilation, and includes a pressure control component capable of varying the pressure within the airtight compartment such that it opposes pressure changes within the chest. The apparatus would be particularly useful in preventing the paradoxical movement of flail chest injuries. The device would also lessen pain experienced by patients with thoracic injuries such as rib fractures and post operative suffering.

20 Claims, 1 Drawing Sheet

Related U.S. Application Data

(60) Provisional application No. 62/119,588, filed on Feb. 23, 2015.

(51) Int. Cl.
    *A61H 31/02*     (2006.01)
    *A61H 31/00*     (2006.01)

(56) References Cited

U.S. PATENT DOCUMENTS

| | | | | |
|---|---|---|---|---|
| 5,738,089 | A | * | 4/1998 | Hoshi .................. A61H 9/0078 128/205.16 |
| 5,820,572 | A | * | 10/1998 | Palmer .................. A61H 31/02 601/44 |
| 6,059,742 | A | * | 5/2000 | Palmer .................. A61H 31/02 601/106 |
| 2016/0324722 | A1 | * | 11/2016 | Sinderby .............. A61H 9/0078 |

\* cited by examiner

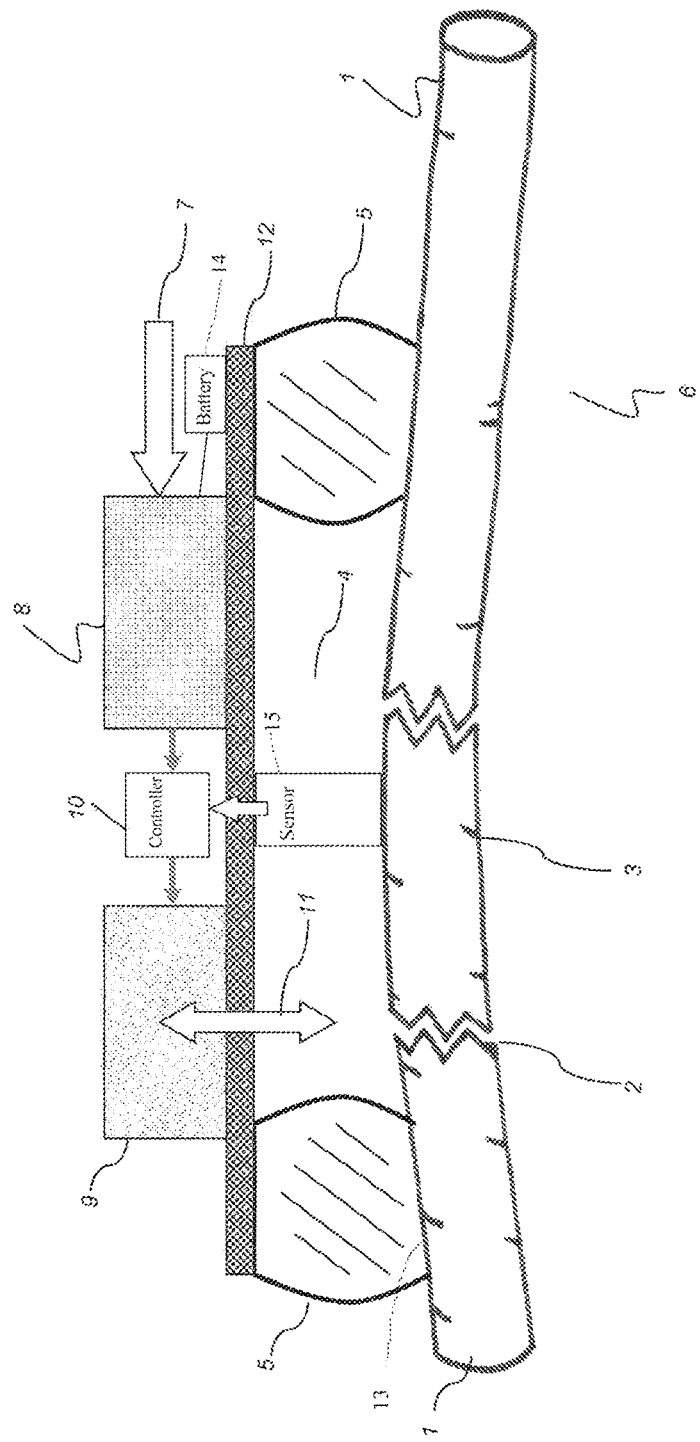

SYSTEM FOR DYNAMICALLY STABILIZING THE CHEST WALL AFTER INJURY, FRACTURE, OR OPERATIVE PROCEDURES

RELATED APPLICATIONS

This application is a continuation application of co-pending U.S. patent application Ser. No. 15/051,383, filed Feb. 23, 2016, entitled A SYSTEM FOR DYNAMICALLY STABILIZING THE CHEST WALL AFTER INJURY, FRACTURE, OR OPERATIVE PROCEDURES, which claims the benefit of U.S. Provisional Application Ser. No. 62/119,588, entitled A SYSTEM FOR DYNAMICALLY STABILIZING THE CHEST WALL AFTER INJURY, FRACTURE, OR OPERATIVE PROCEDURES, filed Feb. 23, 2015, the entire disclosures of each of which applications are herein incorporated by reference.

FIELD OF THE INVENTION

The invention disclosed herein relates in general to the fields of devices used in medicine, surgery and emergency trauma therapy, and in particular to methods for stabilizing the chest wall after injuries such as rib fractures, flail chest, or surgery.

BACKGROUND OF THE INVENTION

The need to create negative intrathoracic pressures so as to allow ventilation has necessitated that the human chest be a rigid structure. This is achieved via the ribs, the spine and connecting cartilage, all of which form components of the thorax. The rigid and semi-rigid component of the thorax may be damaged as a result of injury or operative surgical procedure. Rib fractures may involve one or more than one ribs. Surgical entry into the chest may cause fracture or injury to the ribs or sternum. During ventilation, intrathoracic pressure is alternated between positive and negative pressure so as to achieve air movement. After injury to the chest wall, this phasic change in intrathoracic pressure is associated with pain. This pain may cause splinting and interference with normal ventilation.

Flail chest injury in particular is among the most serious traumatic injuries of the thorax. In Flail chest injury a sufficient number of ribs are broken in multiple locations such that a portion of the chest wall is no long structurally attached to the thorax. It is among the most clinically challenging of chest wall injuries not involving actual penetration. (Ciraulo et al. 466-70)

Flail chest injury is significant in particular because pathologic movement of the free segment may result in additional injury. The ends of the fractured ribs may lacerate intercostal vessels and lung tissue. Injury to the underlying lung may cause and exacerbate pulmonary contusion. Movement of the free segment is very painful to the patient.

Movement of the free segment may be paradoxical to the remainder of the chest wall with ventilation. When the patient inhales and exhales, the uninjured chest wall moves outward and inward respectively. The free segment in flail chest injury may move reciprocally, moving in with inspiration and out with expiration. This paradoxical movement may be particularly painful and will act to exacerbate visceral injuries.

Currently, Flail chest injury is definitively stabilized surgically in the operating room. There is currently no effective noninvasive method or device to treat, or even stabilize, flail chest injury. (Dehghan et al. 462-68)

Rib fractures are among the most common chest wall injuries and are associated with significant morbidity and pain. Cardiac surgery is frequently undertaken via an artificial cut through the sternum called a median sternotomy. Both rib fractures and median sternotomy are painful for patients and this pain is difficult to treat. They are also associated with significant morbidity as the pain associated with each of the components of the ventilatory cycle cause the patient to limit chest wall motion which interferes with pulmonary toilet. Similarly, this pain interferes with the normal sighing required for pulmonary toilet.

The changes in intrathoracic pressure created during inspiration exacerbate the pain of rib fractures, median sternotomy, and flail chest injuries. In the case of flail chest injury the changes in intrathoracic pressure associated with the ventilatory cycle exacerbate movement of the free segment and contribute to further injury.

It is now possible to measure ventilation noninvasively using techniques such as impedance, and plethysmography, among others. Such measurement makes possible dynamic treatment of chest wall injuries in a manner that the device acts to provide force reciprocal to intrathoracic changes in pressure.

PRIOR ART

There is no prior art teaching the local dynamic stabilization of the chest wall by varying of the extra thoracic air pressure. The vast majority of previous devices and methods are limited to direct mechanical stabilization such as is achieved with screw, clamps or direct pressure.

The prior art fails to teach localized treatment of chest wall injuries by creation of an airtight extrathoracic compartment and application of dynamic positive and negative pneumatic counter forces. Additionally, the prior art fails to teach real-time sensing of ventilation as an input to the device controller.

Shaffer (U.S. Pat. No. 8,034,011 B2) teaches dynamic stabilization of only the anterior chest by mechanical pressure applied to the lateral surfaces. He does not teach: localized treatment, creation of an airtight extrathoracic compartment, or application of dynamic positive and negative pneumatic counterforce. Of particular significance, Schaffer teaches away from treatment of conditions other than injury to the anterior chest.

Kochamba (WO1999047085 A1) teaches fixation of tissue and broken bones via a pneumatic bladder. He does not teach: creation of an airtight extrathoracic compartment, sensing of ventilation, or application of dynamic positive and negative pneumatic counterforce.

Others (CN 103431934 A) teach an adjustable air column for fixation or protection of thoracic injury. They do not teach: sensing of ventilation, or application of positive and negative dynamic pneumatic counterforce.

Palmer extensively teaches (US 006059742A, WO 201-515-7154 A1) the use of negative distending force to the anterior chest for purposes such as ventilation. Attachment is adhesive although movement of the device may be pneumatic. He does not teach: creation of an airtight extrathoracic compartment, sensing of ventilation, or application of dynamic positive and negative pneumatic counterforce.

The artificial lungs used during the early to mid 20th century achieved ventilation by varying the extrathoracic pressure of the whole thorax. These were not intended toward the purposes described and none of the related art or literature teaches the current technique.

BRIEF DESCRIPTION OF THE DRAWINGS

For a fuller understanding of the nature of the present invention, reference should be had to the following detailed description and preferred embodiment taken in connection with the accompanying drawing in which:

FIG. 1 is a diagrammatic representation of one embodiment of the method. This FIGURE bisects a stylized cross section of the device placed over a human rib fractured in two locations. Such fractures may represent a component of a flail chest injury.

DETAILED DESCRIPTION OF THE PREFERRED EMBODIMENT

Described is a method for dynamically treating and stabilizing the chest wall after injury or surgery. The device adjusts the air pressure in the region over the injury 2, 3 in a manner reciprocal to the ventilatory respirophasic changes in intrathoracic pressure. This counteracts the intrathoracic forces that exacerbate pain or cause movement of fractures or free segments.

The device is a system that includes a number of components and capabilities that a practitioner of ordinary skill in the art would have little difficulty manufacturing using off-the-shelf components once having been taught the invention:

1. An adjustable stabilizing platform 12 that may be applied to the rib cage 1 of a patient over the chest wall injury, rib fracture 2, flail segment 3 or incision. Other components of the system may be incorporated into this platform. The platform may be adjustable so as to optimize function.

2. The patient-side surface of the device have a bladder or adherent component 5 at its circumferential edge. Application to the chest wall creates an airtight compartment 4 between the platform itself and the thorax.

3. The device may have a component 9 capable of placing this compartment 4 under negative and positive pressure and of rapidly varying the pressure 11 in the enclosed space so as to minimize the pain or paradoxical motion of chest wall injuries, rib fractures 2, flail segments 3 or incisions. Such a component 9 would be likely to be an air pump and associated valves and connecting hoses.

4. The device may have a mechanism 8 for measuring ventilation or, alternatively, receive inputs 7 from any system that measures patient respiration. Ventilation can be measured using multiple existing technologies, in particular electrical impedance and plethysmography.

5. A control system 10 capable, in combination with the pump 9, of varying the patient-side compartment pressure 11 in a manner reciprocal to ventilation induced intrathoracic pressure. Thus, this is a system for dynamically opposing the changes in intrathoracic pressure that accompany ventilation. Such a component 10 is very likely to be a standard electrical control system or computer board. The controller may be adjusted by an operator based on the patient's subjective sense of painful paradoxical movement. The controller is capable of synthesizing inputs from the patient and operator so as to minimize paradoxical chest wall motion.

6. A harness system for stabilization during periods of positive pressure within the airtight compartment 4.

7. A battery 14.

8. A patient side sensor 15 capable of detecting or measuring paradoxical chest wall motion.

A practitioner of ordinary skill in the art would be able to obtain or construct all components of the system once taught the invention, including:

1. The adjustable stabilizing frame or platform 12.

2. The adjustable circumferential component 5, having a pliable and/or adherent material 13 that is applied to the patient side circumference to create an airtight compartment 4.

3. The component or mechanism 9 for varying the pressure 11 within the airtight compartment 4.

4. The component or mechanism 8 for measuring the intrinsic ventilation of the patient.

5. The component or mechanism 8 for receiving inputs 7 from other devices measuring patient ventilation and physiology. Existing technologies such as electrical impedance or plethysmography are readily available for this purpose.

6. The controller 10 that interfaces between the measurement of patient ventilation and the component 9 that varies pressure 11 within the airtight compartment 4.

This disclosure includes a method for treating chest wall injuries, the method comprising: creating a localized airtight compartment external to the chest and fully covering the area of injury; varying the pressure within the compartment real-time so as to provide a dynamic counterforce to the changes in intrathoracic pressure that occur during each ventilatory cycle.

A device can include the real-time sensing of ventilation or chest wall motion and dynamic variation of the pressure within the localized airtight compartment in such a manner that the pressure within the airtight compartment opposes pressure changes within the chest. The device can include real-time sensing of paradoxical flail chest free-segment movement and dynamic variation of the pressure within the localized airtight compartment in such a manner that the pressure within the airtight compartment opposes such paradoxical motion. The device can also incorporate an adherent material on the patient-side surface of the apparatus at its circumference such that an adherent airtight compartment is created between the frame and the thorax. The device can also incorporate an adjustable bladder component on the patient-side surface of the apparatus at its circumference such that the airtight compartment may adjust to chest wall anatomy. The device can also incorporate the capability of receiving input signals from other devices measuring ventilation or chest wall movement. The frame can be adjustable so as to better configure to the shape of the chest wall. The power source can be contained within the device in the form of a battery. The apparatus incorporates a patient side sensor capable of detecting or measuring paradoxical chest wall motion and incorporating that data in the variation of pressure within the airtight compartment. The controller may be adjusted by an operator based on the patient's subjective sense of painful paradoxical movement. The controller can be in the form of general purpose computer and algorithm capable of synthesizing inputs from the patient and operator so as to minimize paradoxical chest wall motion.

Usefulness of the Disclosed Invention

This method and its preferred embodiments are intended to treat injuries to the thorax so as to lessen the pain suffered by the patient or further injury to the chest wall or underlying visceral organs. Once it is appreciated that the invention disclosed herein provides the capability to noninvasively treat or stabilize chest wall injuries, rib fractures, flail segments or incisions, the usefulness will be obvious to anyone with ordinary skill in the art of medicine, surgery or traumatology.

Non-Obviousness

The non-obviousness of the invention herein disclosed is demonstrated by the absence of any similar devices within the medical or intellectual property literature. Additionally, a number of large commercial enterprises produce devices for treatment or stabilization of injuries in prehospital, emergency department, operating room or battlefield settings, none of these companies have disclosed or developed devices or systems such as disclosed herein. None of the prior art or medical literature suggest combination of detecting ventilation associated changes in intrathoracic pressure so as to dynamically counteract it via an extrathoracic pneumatic compartment.

The non-obvious inventive step in discovery of the described method includes understanding that thoracic injuries, such as rib fractures and flail chest segments, may be treated regionally by means of real-time dynamic alteration of extrathoracic air pressure.

OTHER PUBLICATIONS INCORPORATED IN THE CURRENT APPLICATION BY REFERENCE

Ciraulo, D. L., et al. "Flail chest as a marker for significant injuries." J. Am. Coll. Surg. 178 (1994): 466-70.

Dehghan, N., et al. "Flail chest injuries: a review of outcomes and treatment practices from the National Trauma Data Bank." J. Trauma Acute. Care Surg. 76.2 (2014): 462-68.

Modifications

It will be understood that many changes in the details, materials, steps and arrangements of elements, which have been herein described and illustrated in order to explain the nature of the invention, may be made by those skilled in the art without departing from the scope of the present invention.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

What is claimed is:

1. A device for treating chest wall injuries, the device comprising:
a frame adapted to be placed external to a chest and fully covering an area of injury to create a localized airtight compartment;
one or more sensors adapted to sense ventilation or chest wall motion in real time,
a pump configured to vary a pressure within the localized airtight compartment,
a controller adapted to interface between a measurement of patient ventilation and the pump, wherein the controller is adapted to control variation of the pressure within the localized airtight compartment external to the chest in real-time so as to provide a dynamic counterforce to the changes in intrathoracic pressure that occur during each ventilatory cycle, the dynamic counterforce minimizing paradoxical motion of chest wall injuries by dynamically counteracting the changes in intrathoracic pressure.

2. The device of claim 1, wherein the pump dynamically varies the pressure within the localized airtight compartment in such a manner that the pressure within the airtight compartment opposes pressure changes within the chest.

3. The device of claim 1 further comprising an adherent material on a patient-side surface of the frame, the adherent material adapted to adhere to the chest and form the localized airtight compartment between the frame and the chest.

4. The device of claim 1 further comprising an adjustable circumferential component having a pliable material on a patient-side surface of the frame at a circumference of the frame to create the airtight compartment.

5. The device of claim 1 further comprising a paradoxical chest wall motion sensor adapted to sense paradoxical chest wall motion, wherein the pump dynamically varies the pressure within the localized airtight compartment in response to a sensed paradoxical chest wall motion data in such a manner that the pressure within the localized airtight compartment opposes paradoxical chest wall motion.

6. The device of claim 1, wherein the controller is adapted to allow an operator to adjust the pressure within the localized airtight compartment based on a patient's subjective sense of painful paradoxical movement.

7. The device of claim 1, wherein the controller is adapted to integrate inputs from an operator and inputs from the one or more sensors to control variation of pressure within the airtight compartment, wherein the sensors are adapted to sense ventilation, chest wall movement, or paradoxical chest wall movement.

8. A device for treating chest wall injuries, the device comprising:
a frame adapted for creating a localized airtight compartment external to a chest of a patient and fully covering an area of injury, the frame having a pliable circumferential component with an adhesive;
a sensor;
an air pump capable of varying a pressure within the localized compartment, and pump to dynamically vary the pressure within the localized compartment in real-time so to provide a dynamic counterforce to changes in intrathoracic pressure that occur during each ventilatory cycle.

9. The device of claim 8 wherein the sensor is a sensor for detecting ventilation or chest wall motion and, the air pump capable of dynamic variation of the pressure within the localized airtight compartment varies the pressure within the airtight compartment between a positive pressure and a negative pressure so the pressure within the airtight compartment opposes pressure changes within the chest.

10. The device of claim 8 wherein the sensor is a sensor for detecting paradoxical flail chest free-segment movement, and the air pump capable of dynamic variation of the pressure within the localized airtight compartment varies the pressure within the airtight compartment to oppose the paradoxical flail chest free-segment movement.

11. The device of claim 8 further incorporating an adjustable bladder component on the patient-side surface of the device at a circumference of the device such that the airtight compartment is able to adjust to chest wall anatomy.

12. The device of claim 8 further comprising an input receiver capable of receiving input signals from other devices measuring ventilation or chest wall movement.

13. The device of claim 8 wherein the frame is adjustable to configure to a shape of the chest wall.

14. The device of claim 8 further comprising a patient side sensor capable of detecting or measuring paradoxical chest wall motion, and the controller incorporating data from the sensor regarding paradoxical chest wall motion in a variation of pressure within the airtight compartment.

15. The device of claim 8 wherein the controller is adapted to adjust a variation of pressure within the airtight compartment by an operator based on the patient's subjective sense of painful paradoxical movement.

16. The device of claim 8 wherein the controller is adapted to integrate inputs from the sensor and inputs from an operator so as to minimize paradoxical chest wall motion.

17. A device for treating chest wall injuries, the device comprising:
- a localized airtight compartment adapted to be placed external to a chest and fully covering an area of injury;
- a pump adapted to vary a pressure within the localized airtight compartment external to the chest; and
- a controller adapted to control the pump in real-time so as to provide a dynamic counterforce to changes in intrathoracic pressure that occur during each ventilatory cycle, the dynamic counterforce minimizing movement of a flail segment by providing a pressure in the localized airtight compartment that opposes the movement of the flail segment caused by patient breathing.

18. The device of claim 17, further comprising a sensor adapted to sense in real time ventilation or chest wall motion, wherein in response to sensed ventilation or chest wall motion data, the controller is adapted to control the pump to dynamically vary the pressure within the localized airtight compartment in such a manner that the pressure within the airtight compartment opposes pressure changes within the chest.

19. The device of claim 17, further comprising a sensor adapted to sense in real time paradoxical flail chest free-segment movement, wherein in response to sensed paradoxical flail chest free-segment movement data, the controller is adapted to control the pump to dynamically vary the pressure within the localized airtight compartment in such a manner that the pressure within the airtight compartment opposes the paradoxical flail chest free-segment movement caused by patient breathing.

20. The device of claim 17, wherein the controller adapted to be adjusted by an operator based on a patient's subjective sense of painful paradoxical movement.

* * * * *